US009890327B2

(12) United States Patent
Lo et al.

(10) Patent No.: US 9,890,327 B2
(45) Date of Patent: Feb. 13, 2018

(54) PHOSPHORESCENT TRANSITION METAL COMPLEX, ITS PREPARATION AND USE

(71) Applicant: City University of Hong Kong, Kowloon (HK)

(72) Inventors: Kam Wing Kenneth Lo, Kowloon (HK); Hua Wei Liu, Sha Tin (HK); Cho Cheung Lee, Kowloon (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 14/923,523

(22) Filed: Oct. 27, 2015

(65) Prior Publication Data

US 2017/0114275 A1    Apr. 27, 2017

(51) Int. Cl.

| | |
|---|---|
| *G01N 33/84* | (2006.01) |
| *C07F 13/00* | (2006.01) |
| *G01N 21/64* | (2006.01) |
| *G01N 33/58* | (2006.01) |
| *C09K 11/06* | (2006.01) |

(52) U.S. Cl.
CPC .............. *C09K 11/06* (2013.01); *C07F 13/00* (2013.01); *G01N 21/6428* (2013.01); *G01N 33/58* (2013.01); *G01N 33/84* (2013.01); *C09K 2211/188* (2013.01); *G01N 2021/6439* (2013.01)

(58) Field of Classification Search
CPC ..... C09K 11/06; C07F 13/00; G01N 21/6428; G01N 33/58; G01N 33/84

USPC ......................................................... 546/10
See application file for complete search history.

(56) References Cited

PUBLICATIONS

Reuillard; Anal. Chem. 2014, 86, 4409-4415.*
Abo; J. Am. Chem. Soc. 2011, 133, 10629-10637.*
Lo; RSC Adv. 2014, 4, 10560-10585.*
Zhang; Organometallics 2013, 32, 5098-5102.*
Lo; Inorg. Chem. 2005, 44, 6100-6110.*
Lo; Chem. Commun. 2003, 2704-2705.*
Kashanian; Spectrochimica Acta Part A 2012, 86, 351-359.*
Wu; Anal. Chem. 1996, 68, 3688-3696.*

(Continued)

*Primary Examiner* — Daniel Carcanague
(74) *Attorney, Agent, or Firm* — Renner Kenner Greive Bobak Taylor & Weber

(57) ABSTRACT

A phosphorescent transition metal complex especially suitable as sensor for hydrogen peroxide in cells, in particular in mitochondria in live cells, includes a metallic central atom, which is a transition metal, a first ligand with at least one pyridine ring, and a second ligand having at least one pyridine ring and at least one structural component selected from the group of 1,2-diketone moiety and an arylboronate moiety. A method for preparing the metal complex is also disclosed as well as a method of detecting hydrogen peroxide in cells by incubating cells with the transition metal complex. The metal complex shows advantageous intense and long-lived phosphorescence accompanied by exceptional cellular localization properties. The metal complex is highly photostable and highly selective towards hydrogen peroxide, thus, especially suitable for detecting mitochondrial $H_2O_2$.

6 Claims, 12 Drawing Sheets
(3 of 12 Drawing Sheet(s) Filed in Color)

(56) References Cited

PUBLICATIONS

Dorwald; "Side Reactions in Organic Synthesis: A Guide to Successful Synthesis Design" 2005 Wiley-VCH Verlag GmbH & Co. KGaA, Wienheim, chapter 1, pp. 1-16.*
Ghosh; Inorg. Chem. 2007, 46, 9912-9918.*
Zhang; Chem. Eur. J. 2010, 16, 6884-6891.*
Kele; Microchemical Journal 2013, 108, 156-160.*
Ye; Dalton Trans. 2014, 43, 8414-8420.*
Lin; Methods Enzymol. 2013, 526, 19-43.*
Zhang; Biosensors and Bioelectronics 2015, 64, 542-54.6.*

* cited by examiner

PHOSPHORESCENT TRANSITION METAL COMPLEX, ITS PREPARATION AND USE

TECHNICAL FIELD

The present invention provides a phosphorescent transition metal complex especially suitable as sensor for hydrogen peroxide in cells, in particular in mitochondria, as well as its preparation. The invention further provides a method for detecting hydrogen peroxide in a cell, in particular in mitochondria in a live cell, by using said transition metal complex.

BACKGROUND OF THE INVENTION

Hydrogen peroxide ($H_2O_2$) is one of the reactive oxygen species (ROS) and a secondary messenger that plays an important role in many signaling pathways in living organisms. ROS species generally further include for example singlet oxygen, superoxide radical, hydroxyl radical, and hypochlorite. These species are generated and localized in organelles such as mitochondria.

Whilst controlled generation of $H_2O_2$ is beneficial to cell fitness, mal-regulation on the $H_2O_2$ level is associated with the pathogenesis of various diseases. It is related to oxidative stress and causes oxidative damage to intracellular biomolecules. Especially, the $H_2O_2$ level in the mitochondria is of particular importance because abnormal production and accumulation of $H_2O_2$ at this organelle has been linked to serious diseases such as cancer, Alzheimer's, Parkinson's and Huntington's diseases.

Existing and commercially available imaging reagents for $H_2O_2$ are fluorescent organic dyes. Although they show strong fluorescence, their use is limited by several factors including the fact that they do not allow for a selective detection of $H_2O_2$ over other types of ROS species, i.e. they can only detect the presence of total ROS species.

Moreover, they do not allow for an organelle specific detection of $H_2O_2$, i.e. these imaging reagents do not target on specific organelles so that it is difficult to determine which part of the cell/organism has gained an increase in $H_2O_2$ level.

Still further, these imaging reagents have a low photostability which does usually not allow prolonged irradiation usually required for real-time monitoring of $H_2O_2$ levels in cells. Additionally, the emission of commercially used organic dyes is fluorescence in nature which is associated with a short lifetime, namely in the nanosecond timescale, which is, thus, not sufficient for time-resolved and time-gated detection and microscopy such as fluorescence-lifetime imaging microscopy (FLIM). Moreover, existing sensors for $H_2O_2$, namely fluorescent organic dyes, suffer from high photobleaching rates, substantial and undesired self-quenching, and high pH dependence.

Accordingly, there remains a strong need for biosensors with increased selectivity towards ROS-species especially increased selectivity towards $H_2O_2$, suitable photo-stability, and suitable emission behavior which, for example, allow for real-time monitoring and time-resolved and time-gated detection of specific ROS species in specific organelles.

SUMMARY OF THE INVENTION

In a first aspect, the present invention provides a phosphorescent metal complex. Said phosphorescent metal complex comprises a metallic central atom selected from a transition metal. Hence, the phosphorescent metal complex according to the invention is a transition metal complex having a transition metal as metallic central atom.

The metal complex further comprises a first ligand. Said first ligand comprises at least one pyridine ring, wherein the nitrogen atom of said pyridine ring is coordinated to the metallic central atom, i.e. the nitrogen atom of said pyridine ring is bonded to the metallic central atom. Further comprised in the metal complex is a second ligand having at least one pyridine ring and at least one structural component selected from the group of 1,2-diketone moiety and an arylboronate moiety. The nitrogen atom of the pyridine ring of the second ligand is coordinated to the metallic central atom, too.

In a further aspect, the invention provides a method for preparing said metal complex comprising the step of reacting a precursor complex referenced as precursor complex a) with a compound b) in the presence of a reaction solvent. Said precursor complex a) comprises a metallic central atom selected from a transition metal, and a ligand, which ligand comprises at least one pyridine ring, wherein the nitrogen atom of the pyridine ring is coordinated to the metallic central atom. Compound b) comprises at least one pyridine ring and at least one structural component selected from the group of a 1,2-diketone moiety and an arylboronate moiety.

In still another aspect, the present invention refers to a method for detecting hydrogen peroxide in a cell or organelle thereof, comprising incubating the cell with a metal complex described above, exciting said incubated cell at a suitable excitation wavelength and measuring the emission.

A further aspect concerns the use of the phosphorescent metal complex of the present invention for detecting hydrogen peroxide in a cell or organelle thereof, preferably in mitochondria, which preferably includes incubating the cell with said metal complex, exciting the incubated cell at a suitable excitation wavelength and measuring the emission.

Still further in accordance with the invention is a kit for use in a method for detecting hydrogen peroxide in a cell comprising the metal complex of the present invention and auxiliary reagents.

The metal complex of the present invention allows for advantageous intense and long-lived phosphorescence along with exceptional cellular localization properties, especially uptake and localization in mitochondria. Said metal complex also facilitates real-time monitoring of the $H_2O_2$ level and the detection and imaging of live cells by FLIM due to their advantageously long emission lifetimes which allow for much enhanced sensitivity of the detection of $H_2O_2$. The metal complex of the present invention is highly photostable and no undesired self-quenching occurs. Most importantly, the metal complex allows for specifically detecting $H_2O_2$, in particular in mitochondria compared with other organelles, due to its high selectivity towards $H_2O_2$ amongst the other ROS species including tert-butyl hydroperoxide (TBHP), singlet oxygen ($^1O_2^+$), hydroxyl radical (OH.), nitric oxide (NO), superoxide radical ($O_2^-$), or hypochlorite ($ClO^-$). The cellular uptake of the metal complex of the present invention by the live cells further allows for quantitative analysis of the $H_2O_2$ level for example by using inductively coupled plasma mass spectrometry (ICP-MS). Accordingly, the present invention provides a highly effective biosensor for detecting $H_2O_2$ level in live cells.

BRIEF DESCRIPTION OF THE DRAWINGS

The patent or application file contains at least one drawing executed in color. Copies of this patent or patent application

DETAILED DESCRIPTION OF ILLUSTRATIVE EMBODIMENTS

Figure 1:
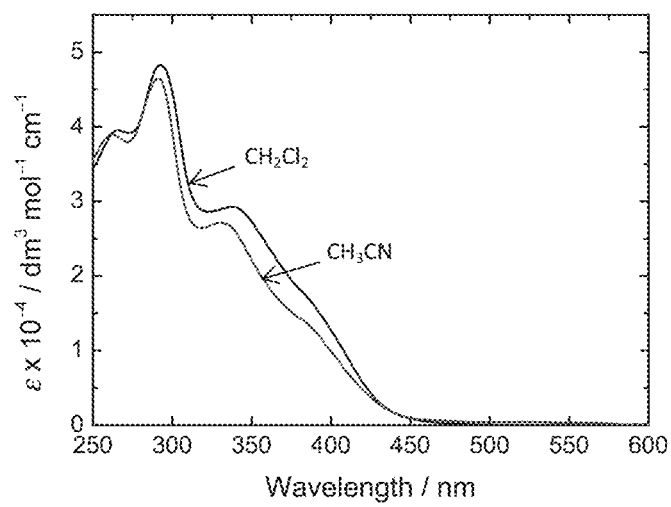
FIG. 1 represents electronic absorption spectra of metal complex of Formula (IV) in $CH_2Cl_2$ and $CH_3CN$ at 298 K (25° C.).

The present invention provides a phosphorescent transition metal complex.

The skilled person is aware of the term "metal complex" also referenced as "coordination complex". Metal complexes consist of a central atom which can be an ion, usually a metallic one, acting as coordination center. Metal complexes further comprise a surrounding array of bound molecules including ions called "ligands", wherein certain atom or atoms in said ligand are coordinated to the central atom and bind to the central atom, respectively (also called "donor atoms").

The term phosphorescence is known to a skilled person, too, and refers to the continuous emission of light from a substance produced after exposure in particular to light. More in detail, said term refers to any substance which temporarily enters an excited state upon exposure to a source of energy, such as light, and emits photons of visible light as they return to a normal state thereby creating a luminescence, or glow, that is still visible after the source of energy has been removed. According to the present invention, the expression "phosphorescent metal complexes" is used for metal complexes and, thus, covers metal complexes which allow for phosphorescence at least after reaction with $H_2O_2$.

In particular, the metal complex of the present invention allows for an emission after reaction with $H_2O_2$, i.e. in the presence of $H_2O_2$, which exceeds, preferably significantly exceeds the emission measurable in the absence of $H_2O_2$.

The metal complex of the present invention comprises
a metallic central atom selected from a transition metal;
a first ligand; and
a second ligand.

The transition metal in said metal complex is preferably selected from rhenium, ruthenium or iridium, more preferably rhenium(I), ruthenium(II), or iridium(III) and most preferably rhenium(I). The use of transition metals, especially of rhenium, ruthenium, and iridium enables cellular uptake of the metal complex of the present invention to be readily quantified by, for example, ICP-MS, which is not possible with commonly used organic dyes.

The first ligand comprises at least one pyridine ring, wherein the nitrogen atom of said pyridine ring is coordinated to the metallic central atom, i.e. said nitrogen atom is a donor atom and binds to the metallic central atom, respectively.

Preferably, the first ligand comprises two pyridine rings, wherein the nitrogen atoms of the at least two pyridine rings are both coordinated to the metallic central atom. Accordingly, the metal complex is preferably a polypyridine metal complex, namely it comprises at least one polypyridine ligand having more than one pyridine ring.

More preferably, the first ligand comprises a phenanthroline, wherein both pyridine rings in said phenanthroline are coordinated to the metallic central atom. Preferably, at least two phenyl moieties are attached to the phenanthroline. In particular, the first ligand is 4,7-diphenyl-1,10-phenanthroline. The inventors found that a metal complex with polypyridine ligands can be easily modified by introducing the second ligand and, thus, such complex is especially preferred.

The second ligand comprises at least one pyridine ring. The nitrogen atom of said pyridine ring of the second ligand is coordinated to the metallic central atom, i.e. said nitrogen atom is a donor atom.

Said second ligand further comprises at least one structural component selected from the group of 1,2-diketone moiety and an arylboronate moiety. A 1,2-diketone moiety is a moiety having Formula (I), whereas an arylboronate moiety is a moiety having a structure of Formula (IIa), wherein either no or at least one substituent may be attached to the phenyl ring, preferably at least one substituent in the ortho-position or the para-position, in particular in the para-position (Formula (IIb)). Presence of at least one of said structural components in the metal complex of the present invention proved to allow for an advantageously high selectivity towards $H_2O_2$. It has been analytically confirmed and is assumed, respectively, that these structural components are able to specifically react with $H_2O_2$ resulting in a cleavage of the 1,2-diketone moiety and arylboronate moiety forming degradation products such as benzoic acid and phenol, respectively.

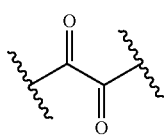

Formula (I)

Formula (IIa)

Formula (IIb)

In especially preferred embodiments, the second ligand comprises at least one 1,2-diketone moiety, more preferably one 1,2-diketone moiety.

Preferably, the second ligand further comprises at least one moiety selected from amine group ($NH_2$) containing moiety, nitro group ($NO_2$) containing moiety or both, in particular the moiety is selected from an amino group, a nitro group or both. Such moieties are preferably attached to a phenyl ring, i.e. the second ligand more preferably further comprises a phenyl ring. In especially preferred embodiments, a phenyl ring having an amino group and a nitro group attached to said phenyl ring, is linked to the at least one pyridine ring of the second ligand by 1,2-diketone linkage. It is assumed that such structure allows for an advantageous specific complex quenching by amine and nitro moieties on the phenyl ring connected to said pyridine by 1,2-diketone linkage. Said quenching is most likely photoinduced electron transfer in nature and, due to said quenching the metal complex is weakly emissive, wherein cleavage of said 1,2-diketone moiety such as through a reaction with $H_2O_2$ leads to a significant enhancement of emission due to departure of aromatic amine and nitro quenching groups from the complex which is highly advantageous when detecting $H_2O_2$.

The metal complex of the invention is preferably a positively charged metal complex, more preferably binding to an anion. Possibly, said positive charge along with the advantageous lipophilicity of the metal complex of the present invention facilitates the uptake of the metal complex in cells and in particular in mitochondria.

In especially preferred embodiments, the metal complex has a structure of Formula (III), which may be referred to as $[Re(Ph_2\text{-phen})(CO)_3(py\text{-}3\text{-}C(=O)C(=O)C_6H_3(NH_2)(NO_2)]^+$:

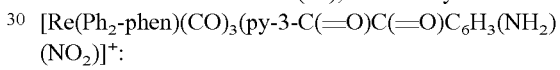

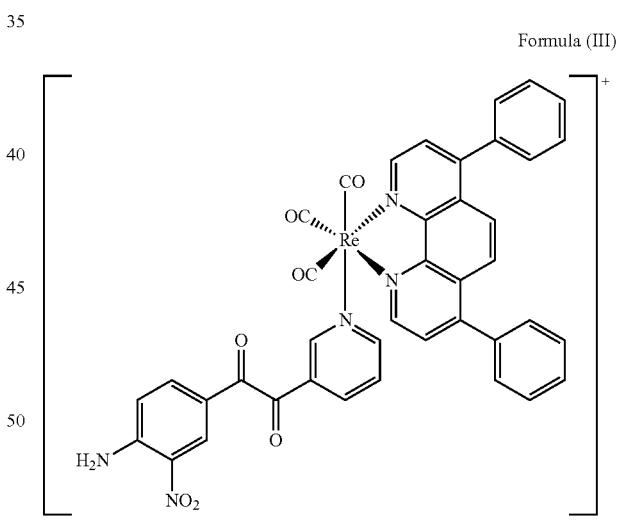

Formula (III)

Also contemplated by the present invention is any suitable salt thereof, i.e. any combination of the metal complex with an anion in particular with an anion selected from the group consisting of trifluoromethanesulfonate, hexafluorophosphate and tetrafluoroborate. In especially preferred embodiments, the anion is trifluoromethanesulfonate.

Hence, most preferably, the metal complex of the present invention corresponds to Formula (IV), which may be referred to as $[Re(Ph_2\text{-phen})(CO)_3(py\text{-}3\text{-}C(=O)C(=O)C_6H_3(NH_2)(NO_2)](CF_3SO_3)$:

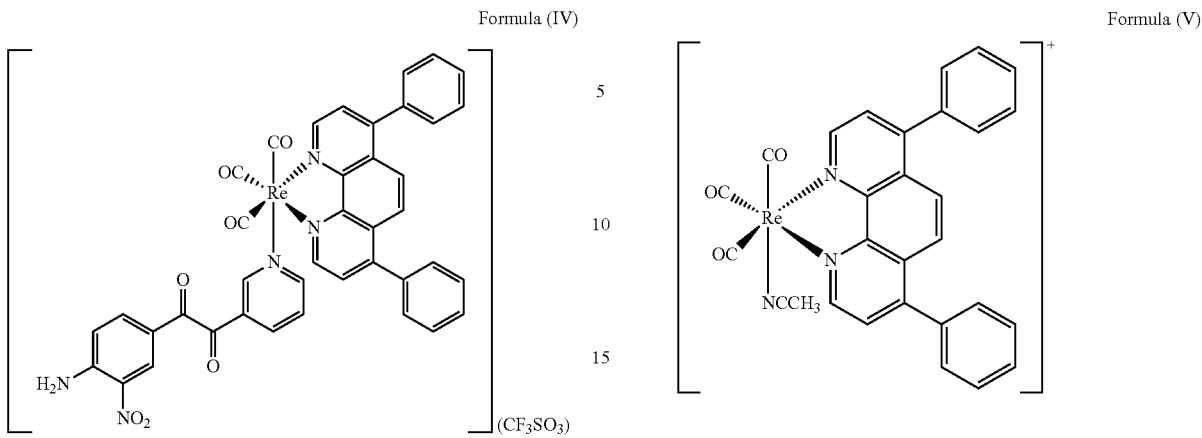

Formula (IV)

Said metal complex proved to be especially selective toward $H_2O_2$ compared to other ROS species including tert-butyl hydroperoxide, singlet oxygen, hydroxyl radical, nitric oxide, superoxide radical, and hypochlorite. Because of the especially advantageous positive charge and lipophilicity said metal complex of Formula (IV) is readily internalized by cells and localized in mitochondria, and, thus, especially suitable as a molecular sensor for mitochondrial $H_2O_2$ for example in live cells.

The present invention also provides a method for preparing the metal complex of the present invention. Said method comprises the step of reacting a precursor complex referred to as precursor complex a) with a compound b) in the presence of a reaction solvent. The precursor complex a) comprises a metallic central atom selected from a transition metal, and a ligand, which ligand comprises at least one pyridine ring, wherein the nitrogen atom of the pyridine ring is coordinated to the metallic central atom. The metallic central atom is preferably selected from rhenium(I), ruthenium(II), and iridium(III), in particular rhenium(I).

Preferably, said precursor complex a) comprises two pyridine rings, wherein the nitrogen atoms of both pyridine rings are coordinated to the metallic central atom. Still more preferably, the ligand is phenanthroline with at least two phenyl moieties attached to phenanthroline. In especially preferred embodiments, the ligand is 4,7-diphenyl-1,10-phenanthroline.

Precursor complex a) preferably comprises a further ligand being $CH_3CN$. Said ligand can be easily substituted by compound b).

In especially preferred embodiments, precursor complex a) has the following Formula (V), which could be referred to as $[Re(Ph_2\text{-phen})(CO)_3(CH_3CN)]^+$:

Formula (V)

This includes suitable salts thereof, i.e. a combination with an anion, in particular selected from the group consisting of trifluoromethanesulfonate, hexafluorophosphate and tetrafluoroborate, especially preferably with trifluoromethanesulfonate. In particular, precursor complex a) corresponds to Formula (VI):

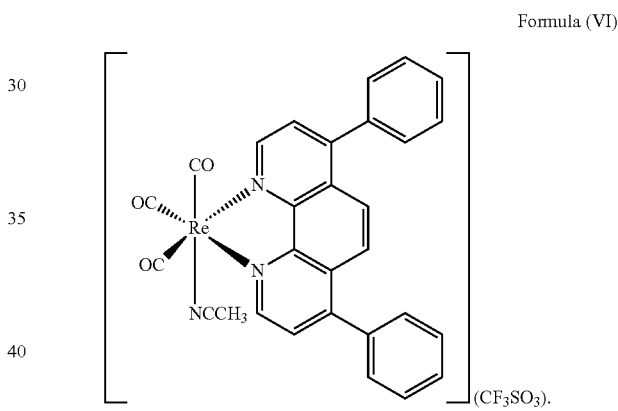

Formula (VI)

Compound b) comprises at least one pyridine ring and at least one structural component selected from the group of a 1,2-diketone moiety and an arylboronate moiety. In especially preferred embodiments, compound b) comprises at least one 1,2-diketone moiety, in particular one 1,2-diketone moiety.

Preferably, compound b) further comprises at least one moiety selected from amine group ($NH_2$) containing moiety, nitro group ($NO_2$) containing moiety or both, in particular the moiety is selected from an amino group, a nitro group or both. Such moieties are preferably attached to a phenyl ring, i.e. compound b) more preferably further comprises a phenyl ring. In especially preferred embodiments, a phenyl ring having an amino and a nitro group attached to said phenyl ring, is linked to the at least one pyridine ring of compound b) by 1,2-diketone linkage.

In especially preferred embodiments, compound b) has the Formula (VII), which could be referred to as 1-(4-amino-3-nitrophenyl)-2-(3-pyridyl)ethane-1,2-dione:

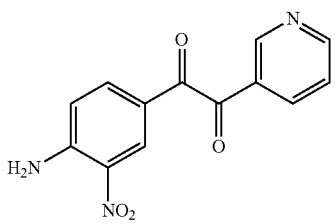

Formula (VII)

The organic solvent of the method of the present invention is preferably a cyclic ether. In particular, the organic solvent is tetrahydrofuran (THF).

The reaction is preferably carried out under reflux conditions. The reaction is preferably carried out under inert atmosphere, preferably under nitrogen atmosphere.

The reaction time is preferably about 12 h, in particular 12 h.

Preferably, the molar ratio of precursor complex a) to compound b) as used in the method of the present invention is about 1:1, in particular 1:1. The term "molar ratio" refers to the ratio of the molar amounts of precursor complex a) and of compound b) as used in the method of the present invention.

In preferred embodiments of the present invention, the method of preparing the metal complex further comprises a step of removing the reaction solvent, more preferably under vacuum, to form a residue which includes the metal complex of the invention.

Preferably, the method of the present invention further comprises at least one purification step, more preferably purification steps a) to c) including:

a) Purifying the residue obtained after removal of the reaction solvent by column chromatography, preferably on silica gel;
b) Eluting the residue obtained from step a) with an eluting solvent;
c) Recrystallizing the metal complex of the invention from a recrystallization solvent.

The eluting solvent is preferably an organic solvent selected from halogenated alkane, aliphatic alkane, cycloalkane, ester, ether, alcohol or a mixture thereof, more preferably a mixture of halogenated alkane and aliphatic alcohol, further preferred dichloromethane with methanol, in particular 20:1 (v/v).

The recrystallization solvent is preferably an organic solvent selected from halogenated alkane, alkane, cycloalkane, ester, ether, alcohol or a mixture thereof, more preferably a mixture of halogenated alkane and aliphatic ether, further preferred dichloromethane with diethyl ether.

In an especially preferred embodiment, the metal complex prepared by the method is the metal complex of Formula (IV) prepared by reacting a precursor complex a) of Formula (VI) with a compound b) of Formula (VII) in a reaction solvent, preferably acyclic ether, more preferably THF. Preferably, the reaction is carried out under reflux conditions. Preferably, in said embodiment the reaction is carried out under an inert atmosphere, preferably under nitrogen. More preferably, the method of preparing the compound of Formula (IV) further comprises steps for preparing the compound of Formula (VII), which preferably comprises the following reaction steps a) to d):

a) Preparing 2-nitro-4-trimethylsilylethynylaniline of Formula (VIII)

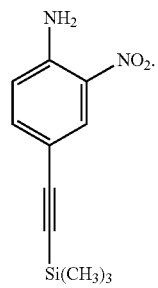

Formula (VIII)

Said reaction step a) preferably comprises reacting 4-bromo-2-nitroaniline, ethynyltrimethylsilane, bis(triphenylphosphine)palladium(II) dichloride, and copper(I) iodide in an organic solvent, in particular triethylamine. Preferably the mixture is refluxed under an inert atmosphere of nitrogen, preferably for at least 12 h, in particular about 24 h; preferably water is added to quench the reaction and still preferably further purification steps are carried out in particular including extraction with dichloromethane, drying over magnesium sulfate, filtration, and solvent removal steps optionally followed by column chromatography.

b) Preparing 4-ethynyl-2-nitroaniline of Formula (IX) from the Compound of Formula (VIII)

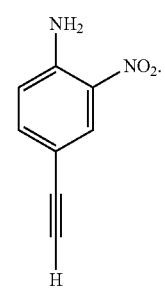

Formula (IX)

Said reaction step b) preferably comprises preparing a mixture of compound of Formula (VIII) with potassium hydroxide and stirring in an organic solvent, in particular in methanol, preferably at room temperature under an inert atmosphere of nitrogen for preferably about 2 h. Preferably, the reaction mixture is neutralized, preferably by using a resin, further preferably by using IR120 H resin, and further purification steps can be carried out in particular including column chromatography and solvent removal steps.

c) Preparing 3-((4-amino-3-nitrophenyl)ethynyl) pyridine (Formula (X)) from the compound of Formula (IX)

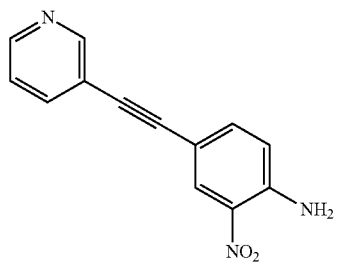

Formula (X)

Said reaction step c) preferably comprises preparing and reacting a mixture of compound of Formula (IX), 3-bromopyridine, bis(triphenylphosphine)palladium(II) dichloride, and copper(I) iodide in a solvent, in particular triethylamine. Preferably, the mixture is refluxed under an inert atmosphere of nitrogen for preferably about 24 h; preferably water is added to quench the reaction and further purification steps may be carried out in particular including extraction with dichloromethane, drying over magnesium sulfate, filtration and solvent removal steps optionally followed by column chromatography.

d) Preparing 1-(4-amino-3-nitrophenyl)-2-(3-pyridyl)ethane-1,2-dione of Formula (VII) from the compound of Formula (X)

Said reaction step d) preferably comprises preparing and reacting a mixture of compound of Formula (X), palladium (II) acetate, and copper(II) bromide in an organic solvent, in particular DMSO. The reaction is preferably carried out at a temperature of at least 100° C., in particular about 120° C. for at least 15 h, in particular for about 20 h. Preferably, water is added to quench the reaction and further purification steps may be carried out in particular including extraction with ethyl acetate, drying over magnesium sulfate, filtration and solvent removal steps optionally followed by column chromatography.

The invention further provides a method for detecting hydrogen peroxide in a cell, preferably in a live cell, or organelle thereof, more preferably for detecting hydrogen peroxide in mitochondria of a cell, in particular of a live cell. The term "cell" as used in the present invention refers to either one cell or more than one cell, i.e. cells, i.e. "cells" are contemplated by said term, too.

Said method for detecting hydrogen peroxide in a cell or organelle thereof comprises the step of incubating said cell with a metal complex of the present invention, exciting the incubated cell at a suitable excitation wavelength and measuring the emission. The skilled person is able to determine a suitable excitation wavelength and to measure the emission.

The incubation is preferably carried out for at least 30 min. The metal complex is preferably added in the form of an incubation solution comprising the metal complex, in particular in a concentration of about 10 μM and especially in a concentration of 10 μM. Preferably, the incubation solution comprises the metal complex and a growth medium, in particular the metal complex and DMEM medium containing DMSO, further preferably the metal complex and DMEM medium containing 1% DMSO (v/v). DMEM, also known as Dulbecco's modified Eagle's medium, is commercially available and known to the skilled person. According to the invention, standard DMEM is used. In other embodiments, a suitable commercially available modified DMEM medium is used. During incubation, the metal complex of the invention preferably reacts with $H_2O_2$ which is associated with an advantageous and significant enhancement of the emission.

In especially preferred embodiments, the metal complex used within said method is the metal complex of Formula (III), in particular the metal complex of Formula (IV):

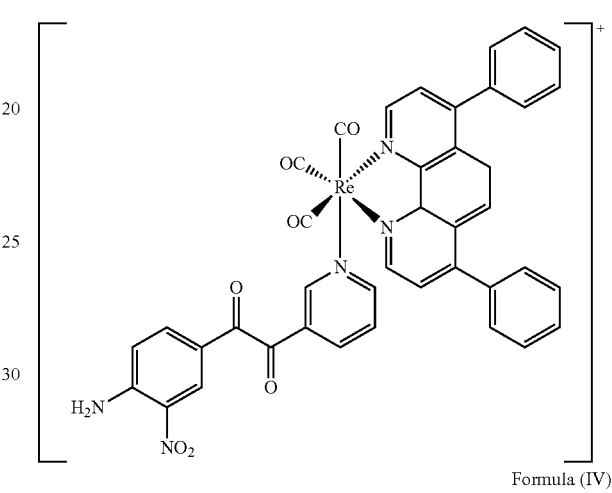

Formula (III)

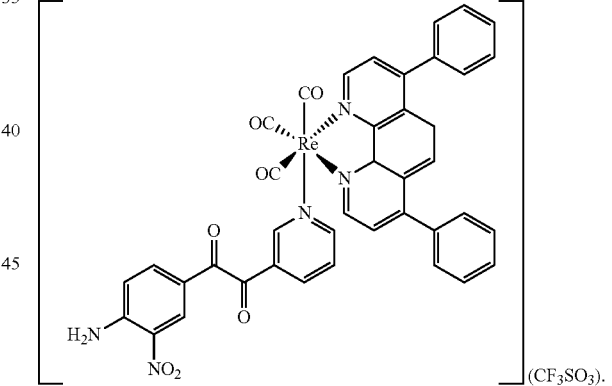

Formula (IV)

The excitation wavelength in said embodiments is preferably 405 nm. The metal complex is used in said embodiments preferably with a concentration of about 10 μM, in particular of 10 μM.

Further in accordance with the invention is a kit for use in a method for detecting hydrogen peroxide in a cell, preferably a live cell, more preferably in mitochondria in a cell, in particular a live cell, comprising the metal complex of the present invention and auxiliary reagents such as a buffer, in particular phosphate buffer, or a growth medium such as DMEM containing 1% DMSO (v/v). Said method preferably comprises the steps referenced above. Most preferably, the metal complex has Formula (III), in particular Formula (IV). The invention further provides the use of the metal complex of the present invention for detecting hydrogen peroxide in a cell, which preferably includes incubating the cell with said metal complex, exciting the incubated cell at a suitable excitation wavelength and measuring the emission.

Also in accordance with the present invention is a method for diagnosis of a disease, which disease is associated with a misregulation in the generation of $H_2O_2$ in cells, in particular in live cells, especially in mitochondria in live cells, said method comprises isolating a sample comprising a cell, measuring the level of $H_2O_2$ by using the metal complex of the present invention, comparing the determined values with a reference value corresponding to a controlled and acceptable generation of $H_2O_2$, respectively, and attributing the deviation to a disease. Also contemplated by the present invention is the use of the metal complex of the present invention for preparing a kit for use in diagnosis of a disease associated with a misregulation in the generation of $H_2O_2$ in cells, in particular in live cells, especially in mitochondria in live cells. Diseases expected to be associated with a misregulation in the generation of $H_2O_2$ in cells, in particular in mitochondria in live cells, include, in particular, cancer, Alzheimer's, Parkinson's, and Huntington's diseases.

The examples set out below further illustrate the invention. The preferred embodiments described above and the drawings as well as examples given below represent preferred or exemplary embodiments and a skilled person will understand that the reference to those embodiments or examples is not intended to be limiting.

EXAMPLES

All solvents were of analytical reagent grade and purified according to standard procedures. Dirhenium decacarbonyl, 4,7-diphenyl-1,10-phenanthroline ($Ph_2$-phen), silver(I) trifluoromethanesulfonate, copper(I) iodide, triethylamine, magnesium sulfate, potassium hydroxide, amberlite IR120H resin, 3-bromopyridine, palladium(II) acetate, copper(II) bromide, hydrogen peroxide ($H_2O_2$), potassium superoxide ($KO_2$), sodium hypochlorite (NaOCl), and ammonium iron (II) sulfate hexahydrate were purchased from Acros. 4-Bromo-2-nitroaniline, ethynyltrimethylsilane, bis(triphenylphosphine) palladium(II) dichloride, tert-butyl hydroperoxide (TBHP), and 3-(4,5-dimethyl-2-thiazolyl)-2,5-diphenyltetrazolium bromide (MTT) were purchased from Aldrich. 3-(2-Hydroxy-1-methyl-2-nitrosohydrazino)-N-methyl-1-propanamine (NOC-7) was purchased from Calbiochem. [Re($Ph_2$-phen)(CO)$_3$($CH_3$CN)]($CF_3SO_3$) was prepared as previously described by Lo and Hui (Lo, K. K. W. and Hui, W. K. Inorg. Chem., 2005, 44:1992-2002). All buffer components were of biological grade and used as received. Autoclaved Milli-Q water was used for the preparation of the aqueous solutions. HeLa cells were obtained from American Type Culture Collection. Dulbecco's modified Eagle's medium (DMEM), phosphate-buffered saline (PBS), fetal bovine serum (FBS), trypsin/ethylenediaminetetraacetic acid (EDTA), penicillin/streptomycin, and MitoTracker Deep Red FM were purchased from Invitrogen. The growth medium for cell culture contained DMEM with 10% FBS and 1% penicillin/streptomycin.

$^1$H NMR spectra were recorded on a Bruker 400 MHz AVANCE III spectrometer at 298 K using deuterated solvents. Chemical shifts (δ, ppm) were reported relative to tetramethylsilane (TMS). Positive-ion electrospray ionization (ESI) mass spectra were recorded on a Perkin Elmer Sciex API 365 mass spectrometer at 298 K. IR spectra of the samples in KBr pellets were recorded in the range of 4000-400 cm$^{-1}$ using a Perkin Elmer FTIR-1600 spectrophotometer. Electronic absorption and steady-state emission spectra were recorded on a Hewlett-Packard 8453 diode array spectrophotometer and a SPEX Fluorolog 3-TCSPC spectrofluorometer, respectively. Emission lifetimes were measured in the Fast MCS or TCSPC mode with a NanoLED N-375 as the excitation source. Unless specified otherwise, all solutions for photophysical studies were degassed with no fewer than four successive freeze-pump-thaw cycles and stored in a 10 cm$^3$ round bottomed flask equipped with a side-arm 1-cm fluorescence cuvette and sealed from the atmosphere by a Rotaflo HP6/6 quick-release Teflon stopper. Luminescence quantum yields were measured by the optically dilute method (Demas, J N., Crosby, G A J., Phys. Chem., 1971, 75:991-1024) using a degassed $CH_3CN$ solution of [Re(phen)(CO)$_3$(pyridine)] ($CF_3SO_3$) (phen=1,10-phenanthroline) ($\varphi_{em}$=0.18, $\lambda_{ex}$=355 nm) as the standard solution.

Example 1

Preparation of the Metal Complex of Formula (IV)

The metal complex of Formula (IV) was prepared by reacting a precursor complex of Formula (VI) with a compound of Formula (VII) in THF as reaction solvent as further described below.

The compound of Formula (VII) was prepared as further described below. The compound of Formula (VI) was prepared as described by Lo and Hui (Lo, K. K. W. and Hui, W. K. Inorg. Chem., 2005, 44:1992-2002).

Example 1A

Preparation of the Compound of Formula (VII)

The compound of Formula (VII) was prepared. Firstly, 2-nitro-4-trimethylsilylethynylaniline of Formula (VIII) was prepared from 4-bromo-2-nitroaniline and ethynyltrimethylsilane. In a further reaction step, 4-ethynyl-2-nitroaniline (Formula (IX)) was prepared from 2-nitro-4-trimethylsilylethynylaniline. In a further step, 3-((4-amino-3-nitrophenyl)ethynyl)pyridine (Formula (X)) was prepared from 4-ethynyl-2-nitroaniline and in another reaction step, the compound of Formula (VII) was prepared from 3-((4-amino-3-nitrophenyl)ethynyl)pyridine.

a) Preparation of 2-nitro-4-trimethylsilylethynylaniline

A mixture of 4-bromo-2-nitroaniline (500.0 mg, 2.31 mmol), ethynyltrimethylsilane (359.0 μL, 2.55 mmol), bis(triphenylphosphine)palladium(II) dichloride (81.3 mg, 0.12 mmol), and copper(I) iodide (44.0 mg, 0.23 mmol) in triethylamine (15 mL) was refluxed under an inert atmosphere of nitrogen for 24 h. Water (10 mL) was added to quench the reaction, and the product was extracted with $CH_2Cl_2$ (50 mL×3). The combined organic layer was dried over magnesium sulfate, filtered, and the solvent was removed under vacuum. The residue was purified by column chromatography on silica gel, and the desired product was eluted with n-hexane/ethyl acetate (20:1, v/v) as the eluent. The solvent was removed under vacuum to afford the product. Yield: 506 mg (93%); $^1$H NMR (300 MHz, CDCl$_3$, 298 K, TMS): δ 8.28 (s, 1H; H3 of aniline), 7.43 (d, 1H, J=8.7 Hz; H5 of aniline), 6.76 (d, 1H, J=8.7 Hz; H6 of aniline), 6.25 (br, 2H; NH$_2$), 0.26 (s, 9H; CH$_3$ of TMS).

b) Preparation of 4-ethynyl-2-nitroaniline

A mixture of 2-nitro-4-trimethylsilylethynylaniline (506.0 mg, 2.16 mmol) and potassium hydroxide (242.0 mg, 4.32 mmol) in $CH_3OH$ (10 mL) was stirred at room temperature under an inert atmosphere of nitrogen for 2 h. The mixture was neutralized using IR120H resin, filtered, and the solvent was removed under vacuum. The residue was purified by column chromatography on silica gel, and the desired product was eluted with n-hexane/ethyl acetate (5:1, v/v) as the eluent. The solvent was removed under vacuum to afford the product. Yield: 360 mg (66%); $^1$H NMR (300 MHz, $CDCl_3$, 298 K, TMS): δ 8.30 (s, 1H; H3 of aniline), 7.45 (d, 1H, J=6.6 Hz; H5 of aniline), 6.78 (d, 1H, J=6.6 Hz; H6 of aniline), 6.26 (br, 2H; $NH_2$), 3.02 (s, 1H; C≡CH).

c) Preparation of 3-((4-amino-3-nitrophenyl)ethynyl)pyridine

A mixture of 4-ethynyl-2-nitroaniline (360.0 mg, 2.22 mmol), 3-bromopyridine (555.7 μL, 2.44 mmol), bis(triphenylphosphine)palladium(II) dichloride (78.0 mg, 0.11 mmol), and copper(I) iodide (42.2 mg, 0.22 mmol) in triethylamine (15 mL) was refluxed under an inert atmosphere of nitrogen for 24 h. Water (10 mL) was added to quench the reaction, and the product was extracted with $CH_2Cl_2$ (50 mL×3). The combined organic layer was dried over magnesium sulfate, filtered, and the solvent was removed under vacuum. The residue was purified by column chromatography on silica gel, and the desired product was eluted with n-hexane/ethyl acetate (10:1, v/v) as the eluent. The solvent was removed under vacuum to afford the product. Yield: 160 mg (30%); $^1$H NMR (300 MHz, DMSO-$d_6$, 298 K, TMS): δ 8.74 (s, 1H; H2 of pyridine), 8.57 (d, 1H, J=3.6 Hz; H6 of pyridine), 8.17 (d, 1H, J=1.8 Hz; H2 of phenyl ring), 7.96 (dt, 1H, J=8.1 and 1.8 Hz; H4 of pyridine), 7.81 (s, 2H; $NH_2$), 7.56 (dd, 1H, J=9.0 and 1.8 Hz; H6 of phenyl ring), 7.48-7.43 (m, 1H; H5 of pyridine), 7.06 (d, 1H, J=9.0 Hz; H5 of phenyl ring); MS (ESI, positive-ion mode): m/z: 240 $[M+H]^+$.

d) Preparation of 1-(4-amino-3-nitrophenyl)-2-(3-pyridyl)ethane-1,2-dione

A mixture of 3-((4-amino-3-nitrophenyl)ethynyl)pyridine (80.0 mg, 0.33 mmol), palladium(II) acetate (7.53 mg, 0.03 mmol), and copper(II) bromide (7.46 mg, 0.03 mmol) in DMSO (3 mL) was heated in an oil bath at 120° C. for 20 h. Water (10 mL) was added to quench the reaction and the mixture was extracted with ethyl acetate (50 mL×3). The combined organic layer was dried over magnesium sulfate, filtered, and the solvent was removed under vacuum. The residue was purified by column chromatography on silica gel, and the desired product was eluted with n-hexane/ethyl acetate (10:1, v/v) as the eluent. The solvent was removed under vacuum to afford the product. Yield: 56 mg (62%); $^1$H NMR (300 MHz, DMSO-$d_6$, 298 K, TMS): δ 9.08 (s, 1H; H2 of pyridine), 8.91 (dd, 1H, J=4.8 and 1.5 Hz; H6 of pyridine), 8.58 (d, 1H, J=1.5 Hz; H2 of phenyl ring), 8.36-8.31 (m, 3H; H4 of pyridine and $NH_2$), 7.96 (dd, 1H, J=9.0 and 1.5 Hz; H6 of phenyl ring), 7.68-7.64 (m, 1H; H5 of pyridine), 7.15 (d, 1H, J=9.0 Hz; H5 of phenyl ring); MS (ESI, positive-ion mode): m/z: 272 $[M+H]^+$.

Example 1B

Preparation of the Compound of Formula (IV)

A mixture of the precursor metal complex of Formula (VI), i.e. of $[Re(Ph_2\text{-phen})(CO)_3(CH_3CN)](CF_3SO_3)$ (163 mg, 0.21 mmol) and compound of Formula (VII), i.e. 1-(4-amino-3-nitrophenyl)-2-(3-pyridyl)ethane-1,2-dione (55.8 mg, 0.21 mmol), in THF (30 mL) was refluxed under an inert atmosphere of nitrogen for 12 h. The solvent was removed under vacuum. The residue was purified by column chromatography on silica gel, and the desired product was eluted with $CH_2Cl_2/CH_3OH$ (20:1, v/v) as the eluent. Recrystallization of the product from $CH_2Cl_2$/diethyl ether afforded metal complex of Formula (IV) as pale yellow crystals. Yield: 150 mg (71%); $^1$H NMR (300 MHz, DMSO-$d_6$, 298 K, TMS): δ 9.74 (d, 2H, J=5.4 Hz; H2 and H9 of $Ph_2$-phen), 9.08 (d, 1H, J=4.8 Hz; H2 of pyridine), 8.53 (d, 1H, J=2.1 Hz; H6 of pyridine), 8.43-8.40 (m, 1H; H4 of pyridine), 8.35 (br, 1H; NH), 8.30 (s, 1H; H2 of phenyl ring), 8.19-8.15 (m, 4H; H3, H5, H6 and H8 of $Ph_2$-phen), 7.76 (dd, 1H, J=9.0 and 2.1 Hz; H6 of phenyl ring), 7.71-7.61 (m, 11H; $C_6H_5$ at C4 and C7 of $Ph_2$-phen and H5 of pyridine), 7.03 (d, 1H, J=9.0 Hz; H5 of phenyl ring); IR (KBr): ν=: 3443 (N—H), 2034 (C≡O), 1933 (C≡O), 1611 (C═O), 1163 ($CF_3SO_3^+$), 1030 ($CF_3SO_3^-$); MS (ESI, positive-ion mode): m/z: 874 $[M-CF_3SO_3^-]^+$

Example 2

Determination of Photophysical Properties of Metal Complex of Formula (IV)

The electronic absorption spectral data of metal complex of Formula (IV) in $CH_2Cl_2$ and $CH_3CN$ at 298 K are listed in Table 1.

TABLE 1

Electronic absorption spectral data of metal complex of Formula (IV) at 298 K

| Solvent | $\lambda_{abs}$/nm (ε/$dm^3$ $mol^{-1}$ $cm^{-1}$) |
|---|---|
| $CH_2Cl_2$ | 265 (42,900), 292 (52,130), 337 (31,140), 389 sh (17,145) |
| $CH_3CN$ | 264 (42,625), 291 (51,810), 331 (30,330), 382 sh (15,820) |

Figure 2:
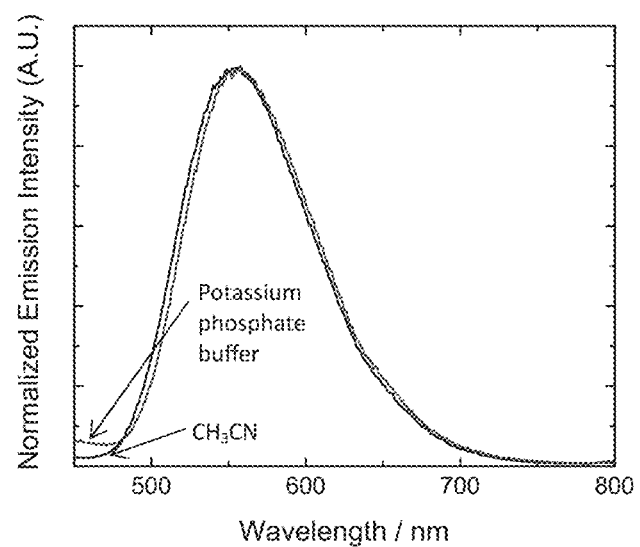
FIG. 2 shows normalized emission spectra of the metal complex of Formula (IV) in $CH_3CN$ and potassium phosphate buffer (50 mM, pH 7.4)/MeOH (7:3, v/v) at 298 K (25° C.).

The electronic absorption spectra of metal complex of Formula (IV) in $CH_2Cl_2$ and $CH_3CN$ at 298 K (25° C.) are shown in FIG. 1. Similar to other rhenium(I) complexes, metal complex of Formula (IV) showed intense absorption bands at ca. 264-337 nm and weaker absorption shoulders at ca. 382-389 nm, which were assigned to spin-allowed intraligand ($^1$IL) (π→π*) (NᴧN and pyridine ligand) and spin-allowed metal-to-ligand charge-transfer ($^1$MLCT) (dπ (Re)→π*(NᴧN)) transitions, respectively. The photophysical data are summarized in Table 2, and the emission spectra of metal complex of Formula (IV) in $CH_3CN$ and aqueous buffer solutions at 298 K are shown in FIG. 2. Upon irradiation, the complex displayed very weak MLCT (dπ (Re)→π*(NᴧN)) emission with luminescence quantum yield <0.007 as a result of photoinduced electron transfer.

TABLE 2

Photophysical data of metal complex of Formula (IV)

| Medium (T/K) | $\lambda_{em}$/nm | $\tau_o$/μs | $\Phi_{em}$ |
|---|---|---|---|
| $CH_3CN$ (298) | 554 | 4.83 | 0.007 |
| Buffer[a] (298) | 557 | 3.14 | 0.005 |

[a]Potassium phosphate buffer (50 mM, pH 7.4)/MeOH (7:3, v/v)

Example 3

Determination of the Reaction Kinetics of Metal Complex of Formula (IV)

Kinetics experiments for the reactions of metal complex of Formula (IV) with $H_2O_2$ were performed under pseudo first-order conditions. Metal complex of Formula (IV) (10 μM) was reacted with $H_2O_2$ in a 1:100, 1:200, 1:400, or 1:800 molar ratio in potassium phosphate buffer (50 mM, pH 7.4)/DMSO (99:1, v/v) at 298 K. The reactions were monitored by UV-Visible spectroscopy at ca. 343 nm. The $k_{obs}$ values were determined by fitting the experimental data to the first-order rate equation, $[A]=[A]_o e^{-kt}$. The $k_2$ value was determined by plotting $k_{obs}$ versus $[H_2O_2]$ and the rate constant corresponds to the determined slope.

Figure 3:
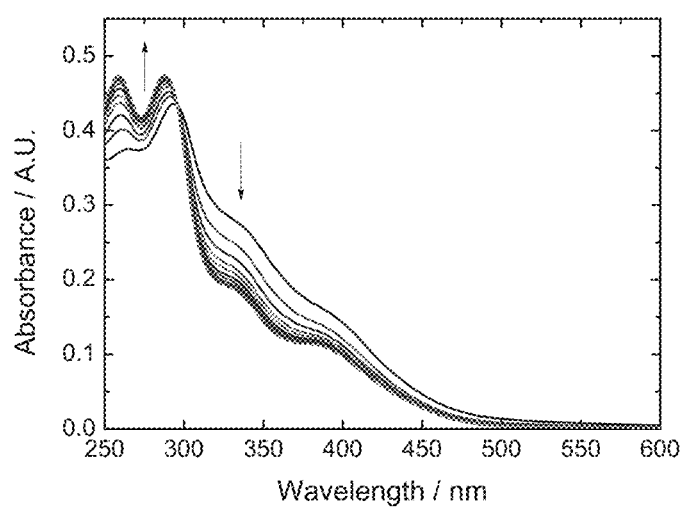
FIG. 3 illustrates the change of absorption spectra of metal complex of Formula (IV) (10 μM) in aerated potassium phosphate buffer (50 mM, pH 7.4)/DMSO (99:1, v/v) at 298 K (25° C.) in the presence of $H_2O_2$ (1 mM); respective arrows indicate the change in absorption with respect to time.
Figure 4:
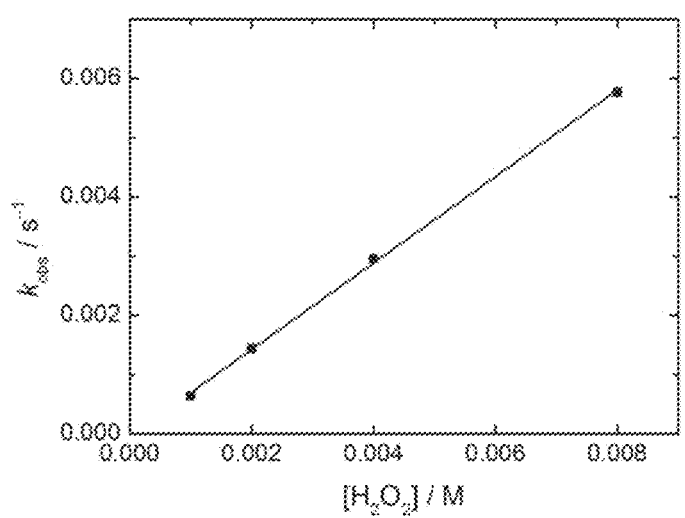
FIG. 4 is a plot of pseudo first-order rate constants of reactions of the metal complex of Formula (IV) with $H_2O_2$ against various concentrations of $H_2O_2$.

The change in absorption spectrum of metal complex of Formula (IV) (10 μM) in aerated potassium phosphate buffer (50 mM, pH 7.4)/DMSO (99:1, v/v) in the presence of $H_2O_2$ (1 mM) at 298 K is shown in FIG. 3. A clear isosbestic point was observed at 296 nm, indicating that the complex was converted to $[Re(Ph_2\text{-phen})(CO)_3(py\text{-3-COOH})]^+$ as the sole product, which was confirmed by $^1H$ NMR spectroscopy. The pseudo first-order rate constant ($k_{obs}$) of reaction of metal complex of Formula (IV) (10 μM) was determined to be $(0.6375\pm0.0092)\times10^{-3}$ $s^{-1}$. The plot of $k_{obs}$ of reactions of metal complex of Formula (IV) with $H_2O_2$ against various concentrations of $H_2O_2$ is shown in FIG. 4. The second-order rate constant was calculated to be $0.7301\pm0.0134$ $M^{-1}$ $s^{-1}$.

Example 4

Determination of Reactivity of Metal Complex of Formula (IV) with $H_2O_2$

In $H_2O_2$-sensing studies, various amounts of $H_2O_2$ (25 mM; 0-20 μL) were added to a series of solutions containing metal complex of Formula (IV) (10 μM) in potassium phosphate buffer (50 mM, pH 7.4)/DMSO (99:1, v/v). The reaction mixtures were incubated in the dark at room temperature for 1.5 h, and their emission spectra were then measured. The limit of detection was determined according to the equation, 30/slope. In the selectivity studies, different reactive oxygen species (100 μM) were added into a series of solutions containing metal complex of Formula (IV) (10 μM) in potassium phosphate buffer (50 mM, pH 7.4)/DMSO (99:1, v/v). The reaction mixtures were incubated in the dark at room temperature for 1.5 h, and their emission spectra were then measured. $H_2O_2$ was diluted from a stabilized 30% aqueous solution. TBHP was diluted from a 70% aqueous solution. NOC-7, $KO_2$, and NaOCl were used as the sources of NO, $O_2^-$, and $ClO^-$, respectively. Singlet oxygen ($^1O_2$) was generated by the reaction of NaOCl and $H_2O_2$ (Held, A M. Et al., Am. Chem. Soc., 1978, 100:5732-5740; Aubry, J M., J. Am. Chem. Soc., 1985, 107:5844-5849). Hydroxyl radicals (OH.) were generated by the reaction of ammonium iron(II) sulfate hexahydrate and $H_2O_2$.

Figure 5:
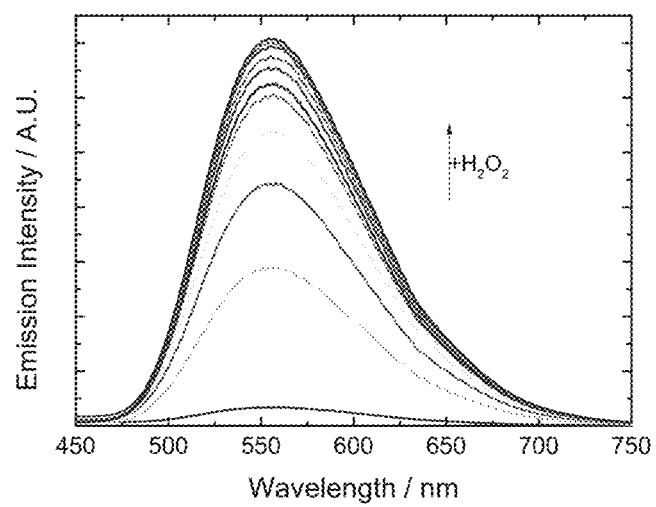
FIG. 5 shows the emission spectral traces of the metal complex of Formula (IV) (10 μM) in aerated potassium phosphate buffer (50 mM, pH 7.4)/DMSO (99:1, v/v) at 298 K (25° C.) in the presence of $H_2O_2$ (0-250 μM); respective arrow indicates the change in emission with increasing amounts of $H_2O_2$.
Figure 6:
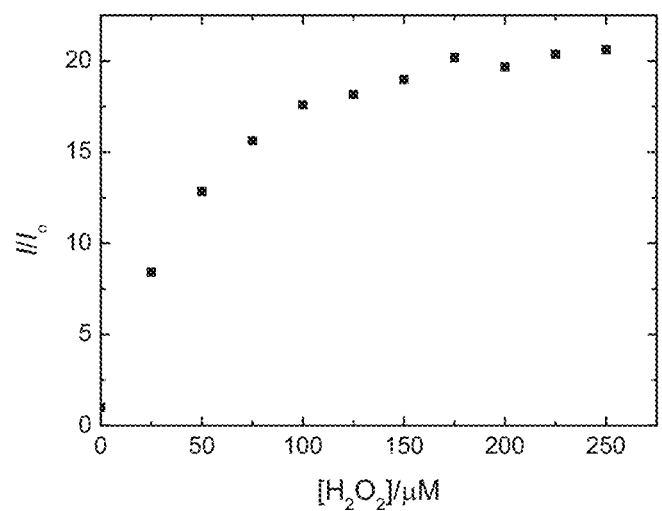
FIG. 6 shows an emission titration curve of metal complex of Formula (IV) (10 μM) in aerated potassium phosphate buffer (50 mM, pH 7.4)/DMSO (99:1, v/v) at 298 K (25° C.) in the presence of $H_2O_2$.

The reactivity of metal complex of Formula (IV) with $H_2O_2$ was examined by emission titrations and the emission titration traces and corresponding titration curve are shown in FIGS. 5 and 6, respectively. Upon addition of $H_2O_2$, metal complex of Formula (IV) showed substantial emission enhancement ($I/I_0$=20.6) at $[H_2O_2]$=250 μM. The emission intensity enhancement showed good linearity with $H_2O_2$ concentrations ranging from 0-50 μM. The detection limit was calculated to be 1.84 μM.

Figure 7:
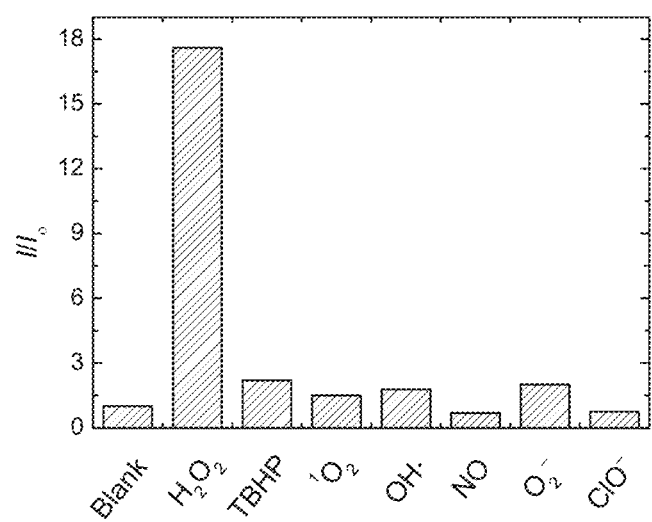
FIG. 7 shows the emission responses of metal complex of Formula (IV) (10 μM) toward $H_2O_2$ (100 μM) and other ROS species (100 μM) in aerated potassium phosphate buffer (50 mM, pH 7.4)/DMSO (99:1, v/v) at 298 K (25° C.).

With respect to the selectivity of metal complex of Formula (IV) toward $H_2O_2$, the emission response of metal complex of Formula (IV) toward various ROS species is shown in FIG. 7. Treatment of metal complex of Formula (IV) with tert-butyl hydroperoxide (TBHP), singlet oxygen ($^1O_2$), hydroxyl radical (OH.), nitric oxide (NO), superoxide radical ($O_2^-$), or hypochlorite ($ClO^-$) did not induce any significant changes in the emission intensity. However, metal complex of Formula (IV) displayed significant emission enhancement after reaction with $H_2O_2$, indicating that it is highly selective toward $H_2O_2$.

Example 5

Cell Viability Studies

To confirm the suitability of the possibility of metal complex of Formula (IV) as phosphorescent sensor for intracellular $H_2O_2$, the cytotoxicity of metal complex of Formula (IV) was examined by the MTT assay.

HeLa cells were cultured in growth medium in a humidified chamber at 37° C. under a 5% $CO_2$ atmosphere. The cells were subcultured every 2-3 days. HeLa cells were seeded in a 96-well flat-bottomed microplate (10,000 cells/well) in a growth medium (100 μL) and incubated at 37° C. under a 5% $CO_2$ atmosphere for 24 h. Metal complex of Formula (IV) (10 μM) and cisplatin (positive control) were then added to the wells with concentrations ranging from ca. $10^{-7}$ to $10^{-4}$ M in a mixture of growth medium/DMSO (99:1, v/v). The wells containing untreated cells were used as blank controls. The microplate was further incubated at 37° C. under a 5% $CO_2$ atmosphere for 48 h. Then MTT in PBS (5 mg/mL; 10 μL) was added to each well. The microplate was then incubated for another 4 h. The medium was removed and DMSO (200 μL) was added to each well. The microplate was further incubated for 10 min. The absorbance of the solutions at 570 nm was measured with a SPECTRAmax 340 microplate reader (Molecular Devices Corp., Sunnyvale, Calif.). Percentage cell survival was calculated relative to the absorbance of the control for each treatment. The viability of untreated cells was assumed to be 100%.

Figure 8:
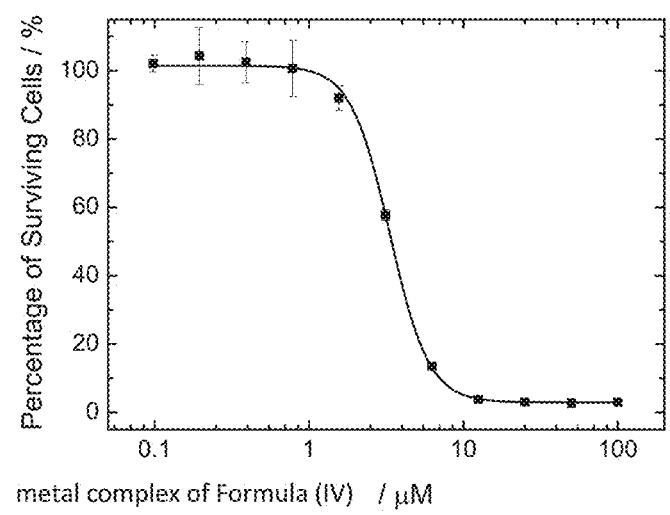
FIG. 8 is a diagram with the percentage of surviving HeLa cells after exposure to metal complex of Formula (IV) for 48 h showing the dose dependence of surviving HeLa cells after exposure.
Figure 9:
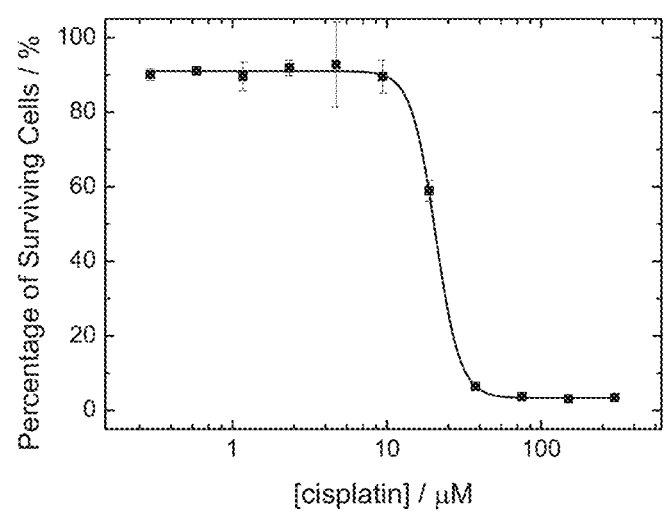
FIG. 9 is a diagram with the percentage of surviving HeLa cells after exposure to cisplatin for 48 h showing the dose dependence of surviving HeLa cells after exposure.

The results indicated the metal complex of Formula (IV) would not cause significant cytotoxic effect under our imaging experiment conditions (10 μM, 1 h, see also Table 3 and FIGS. 8 and 9).

TABLE 3

Cytotoxicity ($IC_{50}$, 48 h) of metal complex of Formula (IV) and cisplatin toward HeLa cells

| Test compound | $IC_{50}$ (μM) |
| --- | --- |
| Metal complex of Formula (IV) | 3.34 ± 0.05 |
| Cisplatin | 20.67 ± 0.56 |

Example 6

Live-Cell Imaging Studies

For co-staining experiments, HeLa cells in growth medium were seeded on a sterilized coverslip in a 35-mm tissue culture dish and grown at 37° C. under a 5% $CO_2$ atmosphere for 48 h. The medium was removed and the cells were incubated with metal complex of Formula (IV) (10 μM) in growth medium/DMSO (99:1, v/v) for 40 min and then with MitoTracker Deep Red FM (100 nM) in a FBS-free medium for another 20 min. Prior to imaging, the cells were washed with PBS (1 mL×3), mounted onto a sterilized glass slide, and then imaged using a Leica TCS SPE confocal microscope with an oil immersion 63× objective. The excitation wavelength for metal complex of Formula (IV) was 405 nm and that of MitoTracker Deep Red FM was 633 nm. The Pearson's coefficient was determined by the program Image J (version 1.45k). For imaging of intracellular $H_2O_2$, HeLa cells in growth medium were seeded on a sterilized coverslip in a 35-mm tissue culture dish and grown at 37° C. under a 5% $CO_2$ atmosphere for 48 h. The medium was removed and the cells were incubated with metal complex of Formula (IV) (10 µM) in growth medium/DMSO (99:1, v/v) for 1 h. The stained cells were washed with PBS (1 mL×3) and further treated with $H_2O_2$ (1 mM) in growth medium for another 2 h. Prior to imaging, the cells were washed with PBS (1 mL×3), mounted onto a sterilized glass slide, and then imaged using a Leica TCS SPE confocal microscope with an oil immersion 63× objective.

Figure 10:
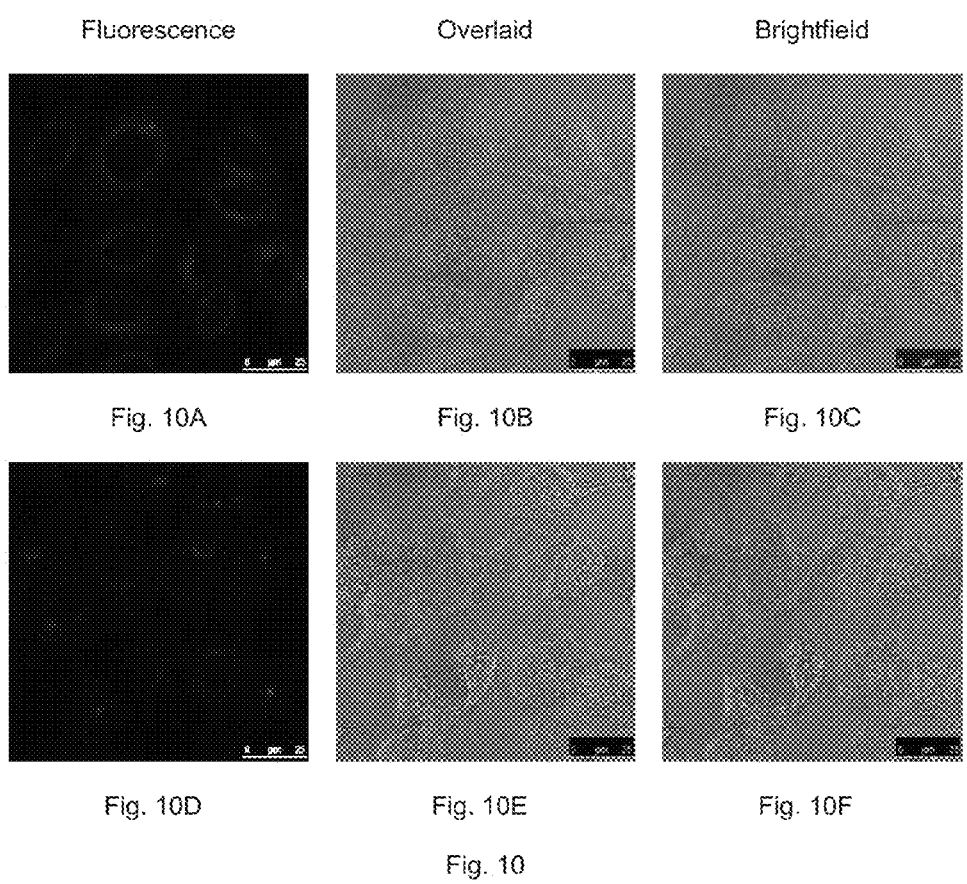
FIGS. 10A, 10B, 10C, 10D, 10E, and 10F provide laser-scanning confocal microscopy images of HeLa cells incubated with a metal complex of Formula (IV) (10 μM) in growth medium/DMSO (99:1, v/v), wherein FIGS. 10A, 10B, and 10C refer to incubation at 37° C. for 1 h, and FIGS. 10D, 10E, and 10F refer to incubation at 4° C. for 1 h.

The use of metal complex of Formula (IV) for intracellular $H_2O_2$-sensing was evaluated by laser-scanning confocal microscopy. HeLa cells loaded with metal complex of Formula (IV) (10 µM) for 1 h showed weak intracellular emission in the perinuclear region (FIG. 10A to 10C). The emission intensity of the cells was significantly reduced when the incubation temperature was lowered to 4° C. (FIG. 10D to 10F). This implies that the internalization of metal complex of Formula (IV) involved an energy-requiring pathway such as endocytosis.

Figures 11, 11A, 11B, 11C:
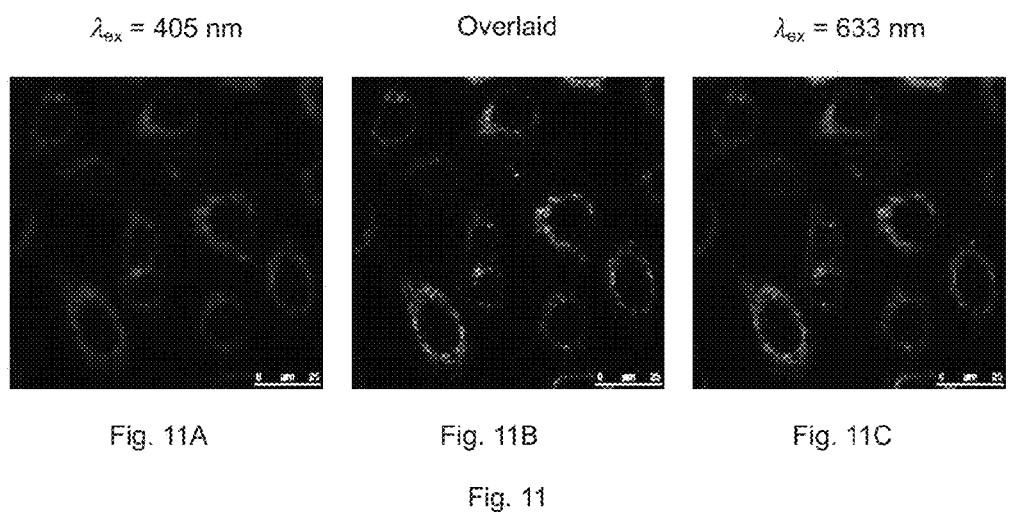
FIG. 11A is a laser-scanning confocal microscopy image of HeLa cells incubated with a metal complex of Formula (IV) (10 μM, 40 min, $\lambda_{ex}$=405 nm) and then MitoTracker Deep Red FM (100 nM, 20 min, $\lambda_{ex}$=633 nm) (Pearson's coefficient: 0.99) in FBS-free medium.
FIG. 11B is a laser-scanning confocal microscopy image of HeLa cells incubated with a metal complex of Formula (IV) (10 μM, 40 min, $\lambda_{ex}$=405 nm) and then MitoTracker Deep Red FM (100 nM, 20 min, $\lambda_{ex}$=633 nm) (Pearson's coefficient: 0.99) in FBS-free medium.
FIG. 11C is a laser-scanning confocal microscopy image of HeLa cells incubated with a metal complex of Formula (IV) (10 μM, 40 min, $\lambda_{ex}$=405 nm) and then MitoTracker Deep Red FM (100 nM, 20 min, $\lambda_{ex}$=633 nm) (Pearson's coefficient: 0.99) in FBS-free medium.
Figure 12:
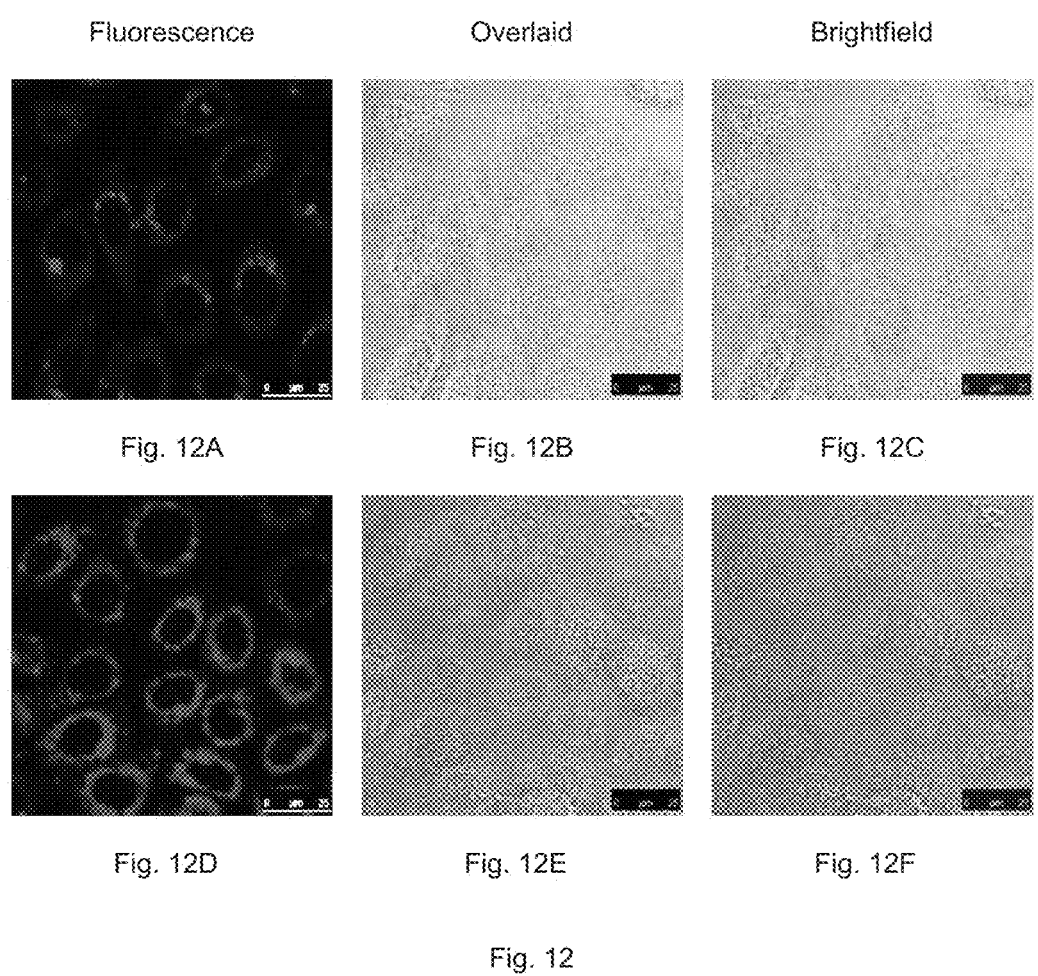
FIGS. 12A, 12B, 12C, 12D, 12E, and 12F each show laser-scanning confocal microscopy images of HeLa cells incubated with a metal complex of Formula (IV) (10 μM) in growth medium/DMSO (99:1, v/v) at 37° C. for 1 h and post-incubated, with FIGS. 12A, 12B and 12C referring to a post-incubation without $H_2O_2$ in growth medium at 37° C. for 2 h, and with FIGS. 12D, 12E, and 12F referring to a post-incubation with $H_2O_2$ (1 mM) in growth medium at 37° C. for 2 h.

With reference to FIG. 11A to 11C, the metal complex of Formula (IV) was localized in the mitochondria (Pearson's coefficient: 0.99). When the complex-stained cells were incubated with $H_2O_2$ (1 mM, 2 h), the intracellular emission intensity was significantly enhanced (FIG. 12A to 12F). Accordingly, metal complex of Formula (IV) is proved to be effective in sensing mitochondrial $H_2O_2$.

The invention claimed is:

1. A phosphorescent metal complex comprising:
   a metallic central atom selected from a transition metal;
   a first ligand comprising at least one pyridine ring, wherein the nitrogen atom of said pyridine ring is coordinated to the metallic central atom;
   a second ligand comprising at least one pyridine ring and at least one 1,2-diketone moiety, wherein the nitrogen atom of said pyridine ring is coordinated to the metallic central atom, wherein the second ligand further comprises an amine group and a nitro group attached to a phenyl ring, and wherein the phenyl ring is linked to said pyridine ring by said 1,2-diketone moiety.

2. The metal complex according to claim 1, wherein said metal complex is a positively charged metal complex binding to an anion.

3. The metal complex according to claim 1, wherein the transition metal is selected from rhenium(I), ruthenium(II), or iridium(III).

4. The metal complex according to claim 1, wherein the transition metal is rhenium(I).

5. The metal complex according to claim 1, wherein the first ligand comprises two pyridine rings, the nitrogen atoms of both pyridine rings are coordinated to the metallic central atom and wherein said first ligand is 4,7-diphenyl-1,10-phenanthroline.

6. The metal complex according to claim 1 having the structure of Formula (IV)

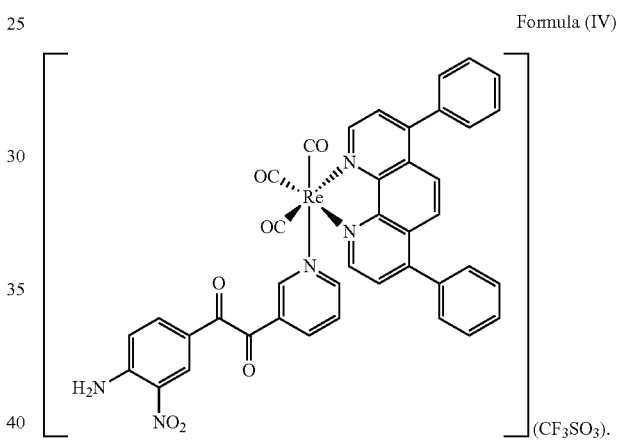

Formula (IV)